(12) United States Patent
Wang et al.

(10) Patent No.: US 7,649,065 B2
(45) Date of Patent: Jan. 19, 2010

(54) FLUOROADAMANTANE DERIVATIVE, FLUORINE-CONTAINING POLYMER AND PRODUCTION METHOD

(75) Inventors: Shu-zhong Wang, Chiyoda-ku (JP); Koichi Murata, Chiyoda-ku (JP); Kazuya Oharu, Chiyoda-ku (JP); Yoshitomi Morizawa, Chiyoda-ku (JP); Osamu Yokokoji, Chiyoda-ku (JP); Naoko Shirota, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 65 days.

(21) Appl. No.: 12/091,846

(22) PCT Filed: Oct. 25, 2006

(86) PCT No.: PCT/JP2006/321298

§ 371 (c)(1),
(2), (4) Date: Apr. 28, 2008

(87) PCT Pub. No.: WO2007/049657

PCT Pub. Date: May 3, 2007

(65) Prior Publication Data

US 2009/0176954 A1  Jul. 9, 2009

(30) Foreign Application Priority Data

Oct. 28, 2005  (JP)  ............................. 2005-314801
Feb. 22, 2006  (JP)  ............................. 2006-045299

(51) Int. Cl.
*C08F 18/20* (2006.01)
(52) U.S. Cl. .................. 526/245; 526/242; 526/244; 526/292.5; 526/309; 526/319; 568/818; 585/352
(58) Field of Classification Search .................. 526/242
See application file for complete search history.

(56) References Cited

U.S. PATENT DOCUMENTS

| | | | |
|---|---|---|---|
| 4,402,984 A * | 9/1983 | Moore | ........................ 514/755 |
| 7,084,295 B2 | 8/2006 | Tanaka et al. | |
| 7,314,952 B2 | 1/2008 | Okazoe et al. | |
| 7,326,512 B2 | 2/2008 | Ogata et al. | |
| 2005/0277785 A1 | 12/2005 | Okazoe et al. | |
| 2005/0288528 A1 | 12/2005 | Okazoe et al. | |
| 2007/0083064 A1 | 4/2007 | Oharu et al. | |
| 2007/0129566 A1 | 6/2007 | Wang et al. | |
| 2008/0086019 A1 | 4/2008 | Okamoto et al. | |
| 2008/0132736 A1 | 6/2008 | Wang et al. | |

FOREIGN PATENT DOCUMENTS

| | | | |
|---|---|---|---|
| JP | 2005089363 A * | 4/2005 | |
| JP | 2006 131879 | 5/2006 | |
| JP | 2006131775 A * | 5/2006 | |
| JP | 2006 137798 | 6/2006 | |
| JP | 2006137798 A * | 6/2006 | |
| WO | 03 055841 | 7/2003 | |
| WO | 2004 052832 | 6/2004 | |
| WO | WO 2004050725 A1 * | 6/2004 | |
| WO | WO 2006077862 A1 * | 7/2006 | |

OTHER PUBLICATIONS

James L. Adcock et al., "Polarized C-H Groups as Novel Hydrogen-Bond Donors in Hydryl-F-aklyl Esters: Unequivocal Examples for the 'Pinchas Effect'", J. Org. Chem., vol. 60, pp. 1999-2002, 1995.
James L. Adcock et al., "Highly Fluorinated Adamantols: Synthesis, Acidities, and Reactivities", J. Org. Chem., vol. 61, pp. 5073-5076, 1996.
James L. Adcock et al., "Synthesis and Nucleophilic and Photochemical Reactions of F-Adamantanone", J. Org. Chem., vol. 57, pp. 4297-4300, 1992.
James L. Adcock, et al., "Aerosol Fluorination of 1-Chloroadamantane, 2-Chloroadamantane, and Methyl 1-Adamantylacetate: A Novel Synthetic Approach to 1- and 2-Substituted Hydryl-, Methyl-, and (Difluoromethyl)-F-Adamantanes", J. Org. Chem., vol. 57, pp. 4749-4752, 1992.
James L. Adcock, et al., "Synthesis of Lithio-F-Adamantanes: The First Documented $^{19}$F NMR Spectrum of a Perfluoroalkyllithium and the Rearrangement of 2-Lithio-F-Adamantane to 1-Lithio-F-Adamantane", J. Org. Chem. vol. 58, pp. 1999-2000, 1993.

* cited by examiner

*Primary Examiner*—Marc S Zimmer
*Assistant Examiner*—Nicole M Buie
(74) *Attorney, Agent, or Firm*—Oblon, Spivak, McClelland, Maier & Neustadt, L.L.P.

(57) ABSTRACT

To provide a novel fluoroadamantane derivative, a novel polymerizable fluoroadamantane derivative and a novel fluoropolymer, and processes for production thereof. To provide the following compound (3), the following compound (4), a polymer obtained by polymerizing the compound (4) and processes for production thereof:

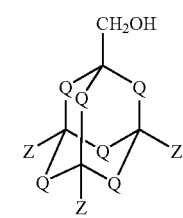

(3)

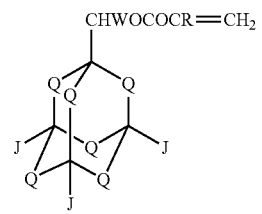

(4)

provided that Q represents —CHF— or —CF$_2$— (provided that six Qs may be the same or different), Z represents —H, —F or —CH$_2$OH (provided that three Zs may be the same or different), W represents —H or a C$_{1-10}$ hydrocarbon group, R represents —H, —F, —CH$_3$ or —CF$_3$, and J represents —H, —F, —CHWOH or —CHWOCOCR=CH$_2$ (provided that three Js may be the same or different).

15 Claims, No Drawings

FLUOROADAMANTANE DERIVATIVE, FLUORINE-CONTAINING POLYMER AND PRODUCTION METHOD

TECHNICAL FIELD

The present invention relates to a novel fluoroadamantane derivative, a novel fluoropolymer and processes for production thereof.

BACKGROUND ART

A fluoroadamantane compound has been known in which among hydrogen atoms in adamantane, a hydrogen atom bonded to a tertiary carbon atom is substituted by a hydroxyl group, a fluorocarbonyl group or a fluoroalkyl carbonyloxy group, and further remaining hydrogen atoms are substituted by fluorine atoms (see Patent Document 1)

Further, Non-Patent Document 1 and Non-Patent Document 2 disclose that a compound represented by the following formula (Ad-I), a compound represented by the following formula (Ad-Br) or a compound represented by the following formula (Ad-Si) is obtained from a reaction intermediate obtained by reacting a compound represented by the following formula (Ad-H) with methyllithium.

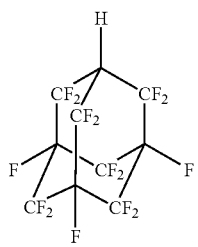
(Ad-H)

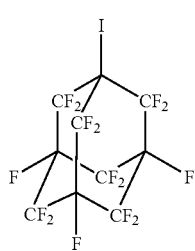
(Ad-I)

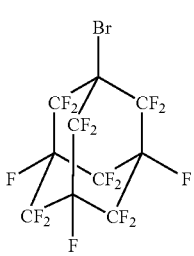
(Ad-Br)

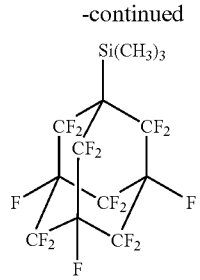
(Ad-Si)

On the other hand, as a radical polymerizable fluoroadamantane, there is a compound in which a hydrogen atom bonded to a tertiary carbon atom in adamantine is directly substituted by a (meth)acryloyloxy group, and further remaining hydrogen atoms are substituted by fluorine atoms, such as a compound represented by the following formula (provided that $R^a$ is a hydrogen atom or a methyl group) (See Patent Document 2).

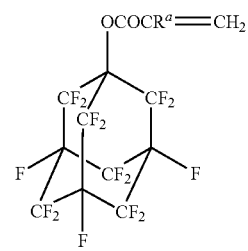

Patent Document 1: WO04/052832
Patent Document 2: WO03/55841
Non-Patent Document 1: J. Org. Chem. 1992, 57, 4749
Non-Patent Document 2: J. Org. Chem. 1993, 58, 1999

DISCLOSURE OF THE INVENTION

Object to be Accomplished by the Invention

However, the reactivity of a fluoroadamantane compound in which a fluorocarbonyl group is bonded to a tertiary carbon atom in adamantine, has not sufficiently been studied. Further, the reactivity of the hydrogen atom in the compound represented by the formula (Ad-H) has not also been studied except for the reaction of the hydrogen atom with $CH_3Li$.

It is desired for a radical polymerizable fluoroadamantane to study various molecular structures, in order to improve the polymerizablity and e.g. properties of the polymer. However, fluoroadamantane practically provided is limited to fluoroadamantane in which a hydrogen atom bonded to a carbon atom in adamantine is directly substituted by a (meth)acryloyloxy group, and a molecular structure thereof has not sufficiently been studied.

Means to Accomplish the Object

The present inventors have conducted studies on the reactivity of a fluorocarbonyl group in fluoroadamantane having the fluorocarbonyl group bonded to a tertiary carbon atom. As a result, they have discovered that the fluorocarbonyl group can readily be substituted by a hydrogen atom. Further, they have conducted studies on the reactivity of a hydrogen atom in fluoroadamantane having the hydrogen atom in a tertiary carbon atom. As a result, they have discovered that the hydrogen atom can readily be substituted by a 1-hydroxy hydrocarbon group. Further, they have discovered a novel fluoroadamantane derivative.

Further, the present inventors have considered that fluoroadamantane in which a hydrogen atom bonded to a tertiary carbon atom in adamantine is substituted by (meth)acryloyloxy group via a connecting group, is highly polymerizable. And as a result of the extensive studies, they have discovered a novel polymerizable fluoroadamantane in which a hydrogen atom bonded to a tertiary carbon atom in adamantine is substituted by (meth)acryloyloxy group and further remaining hydrogen atoms are substituted by fluorine atoms.

Namely, the present invention provides the following:

1. A process for producing a compound represented by the following formula (p2), which comprises reacting a compound represented by the following formula (m1) with a protic nucleophile:

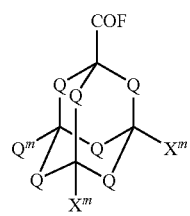
(m1)

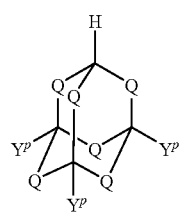
(p2)

provided that the symbols in the formulae have the following meanings:

Q: a monofluoromethylene group or a difluoromethylene group, provided that six Qs may be the same or different;

$X^m$: a hydrogen atom, a fluorine atom or a fluorocarbonyl group, provided that three $X^m$s may be the same or different; and $Y^p$: a group corresponding to each $X^m$, provided that $Y^p$ corresponding to $X^m$ which is a hydrogen atom, is a hydrogen atom, $Y^p$ corresponding to $X^m$ which is a fluorine atom, is a fluorine atom, and $Y^p$ corresponding to $X^m$ which is a fluorocarbonyl group, is a fluorocarbonyl group or a hydrogen atom.

2. A process for producing a compound represented by the following formula (p21), which comprises reacting a compound represented by the following formula (m11) with a protic nucleophile:

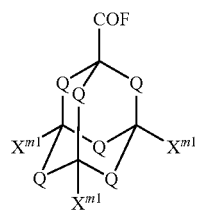
(m11)

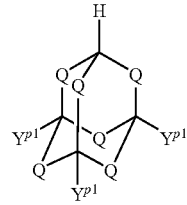
(p21)

provided that the symbols in the formulae have the following meanings:

Q: a monofluoromethylene group or a difluoromethylene group, provided that six Qs may be the same or different;

$X^{m1}$: a hydrogen atom or a fluorine atom, provided that three $X^{m1}$s may be the same or different; and $Y^{p1}$: a group corresponding to each $X^{m1}$, provided that $Y^{p1}$ corresponding to $X^{m1}$ which is a hydrogen atom, is a hydrogen atom, and $Y^{p1}$ corresponding to $X^{m1}$ which is a fluorine atom, is a fluorine atom.

3. The process for producing a compound according to 1 or 2, wherein the protic nucleophile is water.

4. A process for producing a compound represented by the following formula (p3), which comprises reacting a compound represented by the following formula (m2) with a compound represented by the formula W—CHO in the presence of a basic compound:

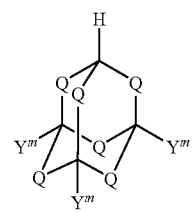
(m2)

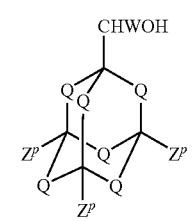
(p3)

provided that the symbols in the formulae have the following meanings:

Q: a monofluoromethylene group or a difluoromethylene group, provided that six Qs may be the same or different;

$Y^m$: a fluorine atom or a hydrogen atom, provided that three $Y^m$s may be the same or different;

$Z^p$: a group corresponding to each $Y^m$, provided that $Z^p$ corresponding to $Y^m$ which is a fluorine atom, is a fluorine atom, and $Z^p$ corresponding to $Y^m$ which is a hydrogen atom, is a hydrogen atom or a group represented by the formula —CHWOH; and W: a hydrogen atom or a $C_{1-10}$ monovalent hydrocarbon group.

5. A process for producing a compound represented by the following formula (p31), which comprises reacting a compound represented by the following formula (m21) with a compound represented by the formula W—CHO in the presence of a basic compound and a polar solvent:

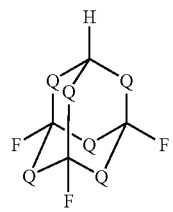

(m21)

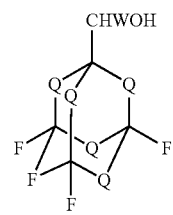

(p31)

provided that the symbols in the formulae have the following meanings:

Q: a monofluoromethylene group or a difluoromethylene group, provided that six Qs may be the same or different; and W: a hydrogen atom or a $C_{1-10}$ monovalent hydrocarbon group.

6. A compound represented by the following formula (3):

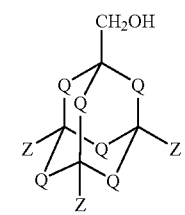

(3)

provided that the symbols in the formula have the following meanings:

Q: a monofluoromethylene group or a difluoromethylene group, provided that six Qs may be the same or different; and Z: a fluorine atom, a hydrogen atom or a hydroxymethyl group, provided that three Zs may be the same or different.

7. A compound represented by the following formula (31):

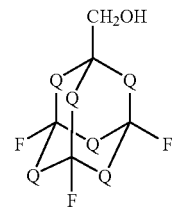

(31)

provided that the symbols in the formula have the following meanings:

Q: a monofluoromethylene group or a difluoromethylene group provided that six Qs may be the same or different.

8. A process for producing a compound represented by the following formula (p4), which comprises reacting a compound represented by the formula $CH_2$=CRCOG with a compound represented by the following formula (m3):

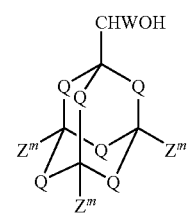

(m3)

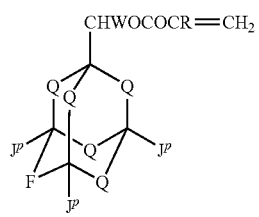

(p4)

provided that the symbols in the formulae have the following meanings:

G: a halogen atom;

W: a hydrogen atom or a $C_{1-10}$ monovalent hydrocarbon group;

R: a hydrogen atom, a fluorine atom, a methyl group or a trifluoromethyl group;

Q: a monofluoromethylene group or a difluoromethylene group, provided that six Qs may be the same or different;

$Z^m$: a hydrogen atom, a fluorine atom or a group represented by the formula —CHWOH, provided that three $Z^m$s may be the same or different; and $J^p$: a group corresponding to each $Z^m$, provided that $J^p$ corresponding to $Z^m$ which is a hydrogen atom, is a hydrogen atom, $J^p$ corresponding to $Z^m$ which is a fluorine atom, is a fluorine atom, and $J^p$ corresponding to $Z^m$ which is a group represented by the formula —CHWOH, is a group represented by the formula —CHWOH or a group represented by the formula —CHWOCOCR=$CH_2$.

9. A compound represented by the following formula (4):

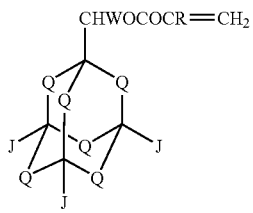
(4)

provided that the symbols in the formula have the following meanings:

W: a hydrogen atom or a $C_{1-10}$ monovalent hydrocarbon group;

R: a hydrogen atom, a fluorine atom, a methyl group or a trifluoromethyl group;

Q: a monofluoromethylene group or a difluoromethylene group, provided that six Qs may be the same or different; and J: a hydrogen atom, a fluorine atom, a group represented by the formula —CHWOH or a group represented by the formula —CHWOCOCR=$CH_2$, provided that three Js may be the same or different.

10. A compound represented by the following formula (41):

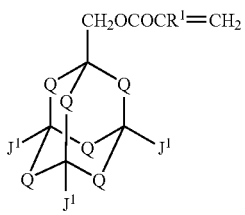
(41)

provided that the symbols in the formula have the following meanings:

$R^1$: a hydrogen atom or a methyl group;

Q: a monofluoromethylene group or a difluoromethylene group, provided that six Qs may be the same or different; and $J^1$: a hydrogen atom or a fluorine atom, provided that three $J^1$s may be the same or different.

11. A polymer obtained by polymerizing a compound represented by the formula (4).

12. A polymer obtained by polymerizing a compound represented by the formula (41).

13. The polymer according to 11 or 12, which has a weight average molecular weight of from 1,000 to 1,000,000.

EFFECTS OF THE INVENTION

According to the present invention, it is possible to provide a novel fluoroadamantane derivative, a novel fluoropolymer, and processes for production thereof. The fluoropolymer of the present invention is excellent in e.g. the heat resistance, mold release properties, chemical resistance, transparency, light resistance, water repellency, oil repellency or low refractive index characteristics.

BEST MODE FOR CARRYING OUT THE INVENTION

In this specification, a compound represented by the formula (m1) will be referred to as a compound (m1). The same also applies to compounds represented by other formulae. Further, an acrylic acid and a methacrylic acid will generally be referred to as a (meth)acrylic acid, an acrylate and a methacrylate will generally be referred to as a (meth)acrylate, and an acryloyl group and a methacryloyl group will generally be referred to as a (meth)acryloyl group.

The present invention provides a process for producing the following compound (p2), which comprises reacting the following compound (m1) with a protic nucleophile:

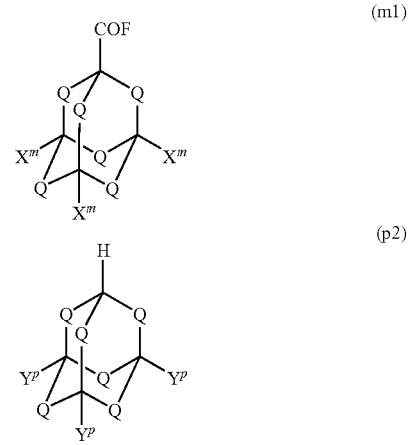

In the compounds in the present invention, six Qs may be the same or different, but at least four Qs may preferably be difluoromethylene groups, and particularly preferably all of the six Qs may be difluoromethylene groups (the same applies hereinafter).

It is preferred that three $X^m$s in the compound (m1) are each independently a fluorine atom or a fluorocarbonyl group.

As specific examples of the compound (m1), the following compounds may be mentioned.

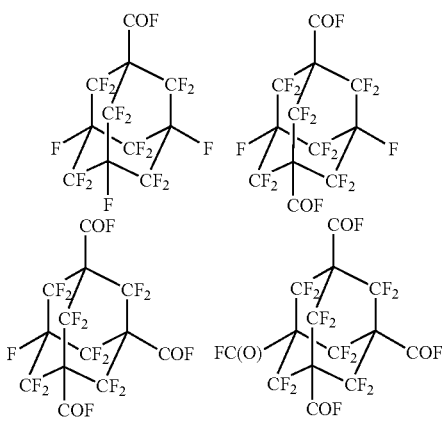

In the compound (p2), $Y^p$ is a group corresponding to each $X^m$. $Y^p$ corresponding to $X^m$ which is a fluorocarbonyl group, is preferably a hydrogen atom. Namely, in the production process of the present invention, it is preferred that all of the fluorocarbonyl groups in the compound (m1) are substituted by hydrogen atoms.

As specific examples of the compound (p2), the following compounds may be mentioned.

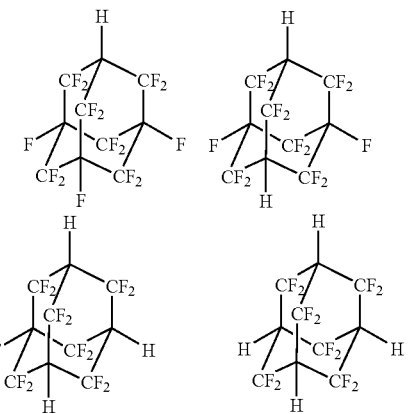

The fluorocarbonyl group bonded to a tertiary carbon atom in the compound (m1) is unexpectedly chemically unstable. It is considered that the fluorocarbonyl group is reacted with a protic nucleophile, followed by decarbonylation, whereby the compound (p2) is produced.

The protic nucleophile means a compound with a proton, which undergoes nucleophilic reaction. The protic nucleophile is preferably ammonia, hydrogen sulfide or water, particularly preferably water. When the protic nucleophile in the reaction is water, the amount of water to the compound (m1) having $k^{m1}$ fluorocarbonyl groups (wherein $k^{m1}$ is an integer of from 1 to 4) is preferably from 1 $k^{m1}$ to 100 $k^{m1}$ times by mol, particularly preferably from 1 $k^{m1}$ to 10 $k^{m1}$ times by mol.

The reaction is preferably carried out in the presence of an organic solvent. The organic solvent may, for example, be diethyl ether, acetone, tetrahydrofuran, dioxane, toluene, xylene, trichlorotrifluoroethane, dichloropentafluoropropane, Fluorinert FC-77 (tradename, manufactured by 3M), Fluoroether E2 (tradename, manufactured by Lancaster Synthesis Inc.), perfluorooctane or perfluorodecalin. The temperature for the reaction is preferably from 0 to 90° C., particularly preferably from 0 to 50° C. The pressure for the reaction is not particularly limited.

One of the preferred embodiments of the production process of the present invention may be a process for producing the following compound (p21), which comprises reacting the following compound (m11) with a protic nucleophile.

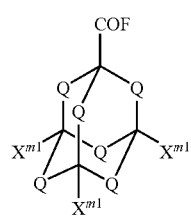

(m11)

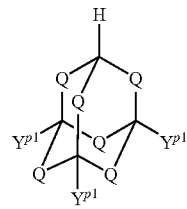

(p21)

The present invention provides a process for producing the following compound (p3), which comprises reacting the following compound (m2) with a compound represented by the formula W—CHO in the presence of a basic compound.

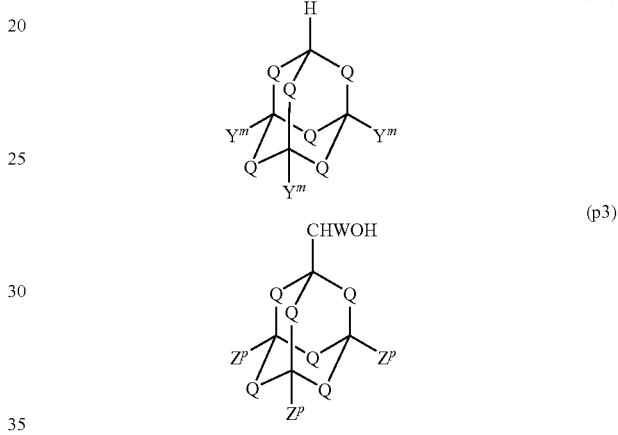

The compound (m2) is preferably the compound (p2) obtained by the above production process, and particularly preferably the compound (p2) in which all of the fluorocarbonyl groups are substituted by hydrogen atoms.

In this specification, W is preferably a hydrogen atom or a $C_{1-7}$ hydrocarbon group, more preferably a hydrogen atom, a $C_{1-7}$ alkyl group or a phenyl group, particularly preferably a hydrogen atom or a $C_{1-7}$ alkyl group from the viewpoint of the reaction yield, furthermore preferably a hydrogen atom or a methyl group, most preferably a hydrogen atom.

As a specific example of the compound represented by the formula W—CHO, formaldehyde, acetaldehyde or benzaldehyde may be mentioned.

In the compound (p3), $Z^p$ is a group corresponding to each $Y^m$. $Z^p$ corresponding to $Y^m$ which is a hydrogen atom, is preferably a group represented by the formula —CHWOH. Namely, in the production process of the present invention, it is preferred that all of hydrogen atoms bonded to tertiary carbon atoms in the compound (m2) are substituted by the groups represented by the formula —CHWOH.

The hydrogen atom bonded to the tertiary carbon atom in the compound (m2) has a high acidity due to an influence of a monofluoromethylene group or a difluoromethylene group adjacent to the tertiary carbon atom. Accordingly, it is considered that the hydrogen atom is readily dissociated into a proton by a basic compound, and further an anion species produced by dissociation of the proton from the compound (m2), is reacted with the compound represented by the formula W—CHO, whereby the compound (p3) is produced.

The basic compound is preferably an alkali metal hydroxide (e.g. sodium hydroxide or potassium hydroxide) or an organic metal basic compound (e.g. butyllithium, methyllithium, phenyllithium, methylmagnesium iodide, ethylmagnesium bromide or phenylmagnesium bromide), particularly preferably an alkali metal hydroxide.

When the basic compound is an alkali metal hydroxide, the reaction temperature is preferably from 50 to 120° C., particularly preferably from 60 to 100° C. The reaction pressure is not particularly limited. Further, when the basic compound is an organic metal basic compound, the reaction temperature is preferably from −80 to 0° C., particularly preferably from −80 to −40° C. The reaction pressure is not particularly limited.

The reaction is preferably carried out in the presence of a polar solvent. The polar solvent is preferably selected from known organic polar solvents. When the basic compound is an alkali metal hydroxide, methanol, ethanol, 2-propanol, dimethylsulfoxide or N,N-dimethylformamide is preferred. Further, a mixed solvent of such organic solvents and water may be used. When the basic compound is an organic metal basic compound, diethyl ether, tetrahydrofuran or dioxane is preferred.

One of the preferred embodiments of the production process of the present invention may be a process for producing the following compound (p31), which comprises the following compound (m21) with a compound represented by the formula W—CHO in the presence of a basic compound and a polar solvent.

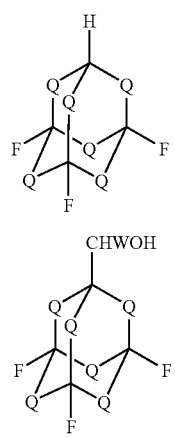

According to the production process of the present invention, it is possible to produce a fluoroadamantane derivative having a group represented by the formula —CHWOH bonded to a tertiary carbon atom in adamantane.

The present invention provides the following compound (3):

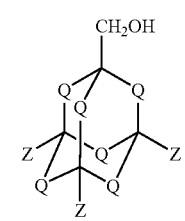

In the compound (3), three Zs are each independently preferably a fluorine atom or a hydroxymethyl group.

The compound (3) is preferably the following compound (31):

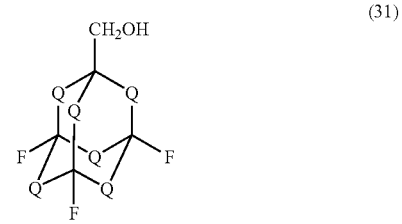

As specific examples of the compound (3), the following compounds may be mentioned:

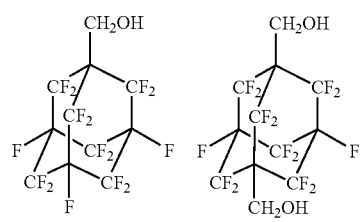

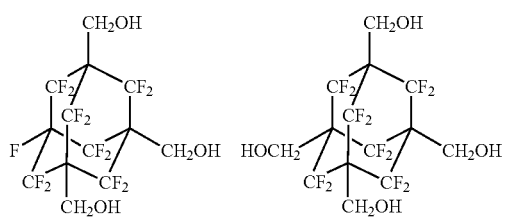

The compound (3) is a novel compound with a structure characterized by having a hydroxymethyl group bonded to a tertiary carbon atom in adamantane. Since the hydroxymethyl group in the compound (3) has a high reactivity, it is possible to produce various adamantane derivatives by reacting the compound (3) with a compound having a functional group capable of reacting with a hydroxyl group. The functional group capable of reacting with a hydroxyl group may be a carboxyl group or its derivative, or an isocyanate group.

For example, it is possible to produce a (fluoroadamantanemethyl) ester by subjecting the compound (3) to esterification reaction with a carboxylic acid or is its derivative. Further, it is possible to produce a polyester by subjecting the compound (3) having at least two hydroxymethyl groups to esterification reaction with a polycarboxylic acid or its derivative having at least two carboxyl groups. The polyester is excellent in e.g. the heat resistance, mold release properties, chemical resistance, transparency, light resistance or low refractive index characteristic.

The present invention provides a process for producing the following compound (p4), which comprises reacting a compound represented by the formula $CH_2$=CRCOG with the following compound (m3):

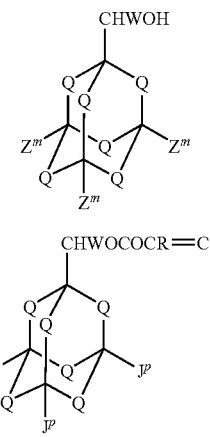

(m3)

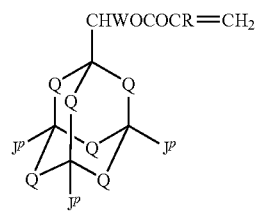

(p4)

G is preferably a chlorine atom or a bromine atom;

R is preferably a hydrogen atom or a methyl group;

$Z^m$ is preferably a fluorine atom or a group represented by the formula —CHWOH; and $J^p$ is a group corresponding to each $Z^m$, provided that $J^p$ corresponding to $Z^m$ which is a group represented by the formula —CHWOH is preferably a group represented by the formula —CHWOCOCR=CH$_2$.

As a specific example of the compound represented by the formula CH$_2$=CRCOG, CH$_2$=CHCOCl, CH$_2$=CHCOBr, CH$_2$=C(CH$_3$)COCl, CH$_2$=C(CH$_3$)COBr, CH$_2$=CFCOCl, CH$_2$=CFCOBr, CH$_2$=C(CF$_3$)COC$_l$ or CH$_2$=C(CF$_3$)COBr may be mentioned.

The above reaction is preferably carried out in accordance with a known method. The hydroxyl group in the compound (m3) is considered to be highly reactive since such a group is bonded to a carbon atom in adamantane via an alkylene group. Accordingly, the production process of the present invention can be carried out at a high reaction yield.

In the above reaction, it is preferred that $1 \times k^{m3}$ to $2 \times k^{m3}$ times by mol of the compound represented by the formula CH$_2$=CRCOG is reacted with 1 mol of the compound (m3) having $k^{m3}$ groups ($k^{m3}$ is an integer of from 1 to 4) represented by the formula —CHWOH.

According to the production process of the present invention, it is possible to provide a novel polymerizable fluoroadamantane derivative in which a hydrogen atom bonded to a tertiary carbon atom in adamantane is substituted by a (meth) acryloyloxy group via a connecting group (a group represented by the formula —CHW—). The present invention provides the following compound (4):

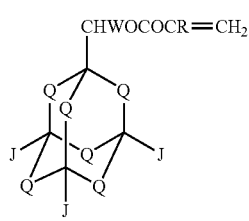

(4)

It is preferred that three Js are each independently a group represented by a fluorine atom or a group represented by the formula —CHWOCOCR=CH$_2$.

The above group is preferably —CH$_2$OCOCH=CH$_2$, —CH(CH$_3$)OCOCH=CH$_2$, —CH$_2$OCOO(CH$_3$)=CH$_2$ or —CH(CH$_3$)OCOC(CH$_3$)=CH$_2$, particularly preferably —CH$_2$OCOOH=CH$_2$ or CH$_2$OCOC(CH$_3$)=CH$_2$.

As preferred embodiments of the compound (4), the following compound (41) and the following compound (42) may be mentioned.

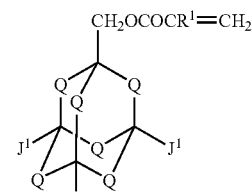

(41)

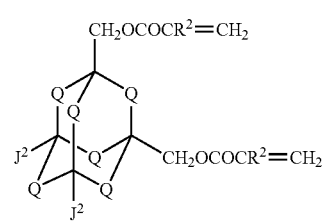

(42)

$R^2$ is a hydrogen atom or a methyl group; and $J^2$ is a hydrogen atom or a fluorine atom, provided that two $J^2$s may be the same or different.

Three J's in the compound (41) and two $J^2$s in the compound (42) are preferably fluorine atoms.

As specific examples of the compound (4), the following compounds may be mentioned:

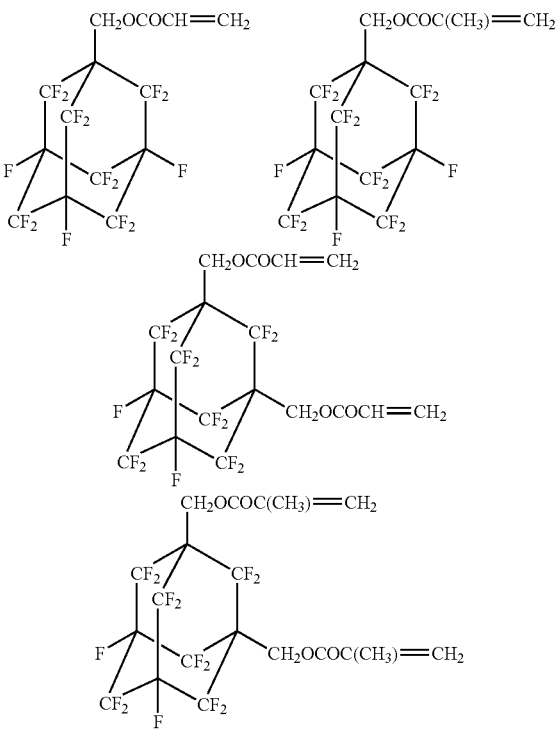

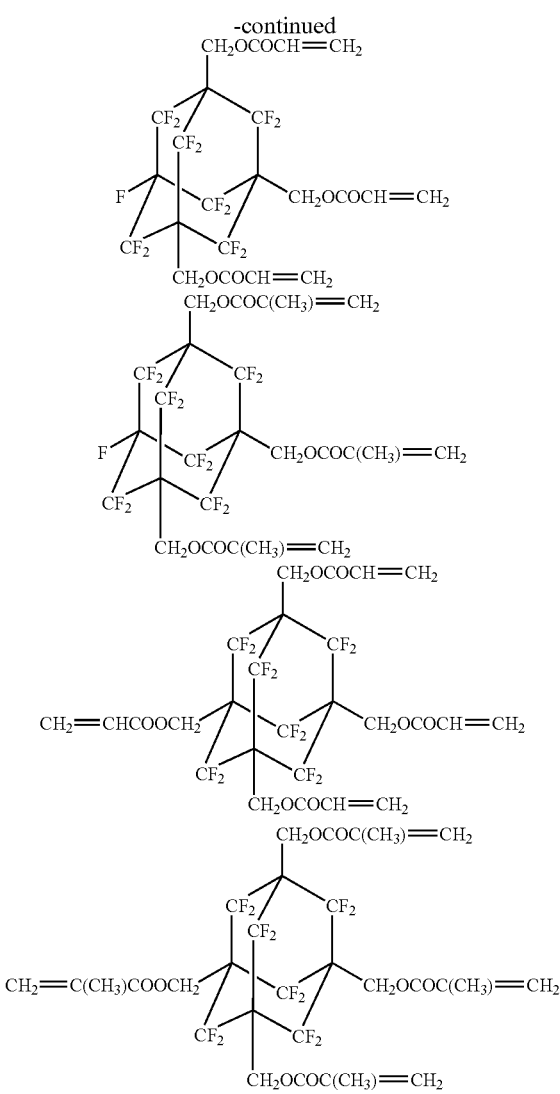

The compound (4) of the present invention is a compound in which a hydrogen atom bonded to a tertiary carbon atom in adamantane is substituted by a group represented by the formula —CHWOCOCR=CH$_2$, and remaining hydrogen atoms are substituted by fluorine atoms. It is considered that the group represented by the formula —CHWOCOCR=CH$_2$ in the compound (4) has a high degree of freedom, and the compound (4) has a high polymerizability. The compound (4) is useful as a polymerizable monomer. By polymerizing the compound (4), it is possible to produce a novel fluoropolymer.

The present invention provides a polymer obtained by polymerizing the compound (4). The weight average molecular weight of the polymer of the present invention is not particularly limited, but is preferably from 1,000 to 1,000,000.

The polymer of the present invention may be a homopolymer obtained by homopolymerizing only the compound (4), or a copolymer obtained by copolymerizing the compound (4) with at least one of other monomers copolymerizable with the compound (4). In the latter case, it is preferred that the polymer of the present invention contains from 0.1 to 99.9 mol % of repeating units formed by polymerization of the compound (4) and further contains from 0.1 to 99.9 mol % of repeating units formed by polymerization of such at least one of other monomers, based on all repeating units.

Such at least one of other monomers is not particularly limited, but a (meth)acrylate other than the compound (4), an unsaturated carboxylic acid amide, a styrene, a vinyl silane, an olefin, a fluoroolefin, a chloroolefin, a vinyl ester, a vinyl ether, a (meth)acrylic acid or an acrylonitrile may be mentioned.

As a specific example of the (meth)acrylate, an acyclic alkyl (meth)acrylate such as methyl (meth)acrylate, ethyl (meth)acrylate, butyl (meth)acrylate, 2-ethylhexyl (meth)acrylate, isooctyl (meth)acrylate, isononyl (meth)acrylate, decyl (meth)acrylate, octadecyl (meth)acrylate, diethylaminoethyl (meth)acrylate, 2-hydroxyethyl (meth)acrylate or 2-hydroxypropyl (meth)acrylate; or a cyclic alkyl (meth)acrylate such as 1-adamantyl (meth)acrylate, 3-hydroxyl-1-adamantyl (meth)acrylate, 2-methyl-2-adamantyl (meth)acrylate, 2-ethyl-2-adamantyl (meth)acrylate, 2-propyl-2-adamantyl (meth)acrylate, 2-butyl-2-adamantyl (meth)acrylate, 2-oxotetrahydrofuran-3-yl (meth)acrylate, glycidyl (meth)acrylate or benzyl (meth)acrylate, may be mentioned.

As a specific example of the unsaturated carboxylic acid amide, acrylamide, itaconic acid diamide, α-ethylacrylamide, crotonic acid amide, fumaric acid diamide, maleic acid diamide, N-butoxymethylacrylamide or N-methylol acrylamide may be mentioned.

As a specific example of the styrene, styrene, α-methylstyrene, chlorostyrene or hydroxystyrene may be mentioned.

As a specific example of the vinyl silane, vinyl methyl dimethoxysilane, vinyl methyl diethoxysilane, vinyl methyl dichlorosilane, vinyl trimethoxysilane, vinyl triethoxysilane or vinyl trichlorosilane may be mentioned.

As a specific example of the olefin, ethylene, propylene or isobutylene may be mentioned.

As a specific example of the fluoroolefin, an acyclic fluoroolefin such as vinyl fluoride, vinylidene fluoride, tetrafluoroethylene, hexafluoropropylene or perfluoro(butenyl vinyl ether); or a cyclic fluoroolefin such as perfluoro(2,2-dimethyl-1,3-dioxole) or perfluoro(2-methylene-1,3-dioxolane) may be mentioned.

As a specific example of the chloroolefin, vinyl chloride, vinylidene chloride or chloroprene may be mentioned.

As a specific example of the vinyl ester, vinyl acetate, vinyl propionate, allyl methyl dimethoxysilylpropyl phthalate or allyl trimethoxysilylpropyl phthalate may be mentioned.

As a specific example of the vinyl ether, 2-hydroxy vinyl ether or aminoethyl vinyl ether may be mentioned.

The method of polymerizing the compound (4) may be a method of polymerizing the compound (4) as it is or a method of polymerizing the compound (4) after the compound (4) is dispersed/dissolved in an organic solvent to prepare a solution composition. From the viewpoint of the operation efficiency, the latter is preferred. The content of the compound (4) in the solution composition is preferably from 0.001 to 50 mass %, more preferably from 0.01 to 50 mass %, particularly preferably from 0.1 to 20 mass %.

As the organic solvent, a perfluoroalkylamine such as perfluorotripropylamine or perfluorotributylamine; a fluorine type organic solvent such as Fluorinert (manufactured by 3M) or Vertrel (manufactured by DU PONT.); or a non-fluorine type organic solvent (a hydrocarbon, an alcohol, a ketone, an ether, an ester, a chlorinated hydrocarbon or the like) may be mentioned. The organic solvents may be used alone or in combination as a mixture of two or more of them.

It is preferred that the compound (4) is polymerized in the presence of a polymerization initiator. The polymerization initiator is preferably used in an amount of from 0.01 to 5 mass %, particularly preferably from 0.5 to 2.5 mass % to the compound (4).

The polymerization initiator may be a thermosensitive polymerization initiator or a photosensitive polymerization initiator. As a specific example of the polymerization initiator, a radical generator is preferred, and a peroxide, an azo compound or a persulfate is particularly preferred.

As a specific example of the azo compound, azobisisobutyronitrile may be mentioned.

As a specific example of the peroxide, $(C_6H_5COO—)_2$, $(C_6F_5COO—)_2$, $(C_3F_7COO—)_2$, $((CH_3)_3CCOO—)_2$, $((CH_3)_2CHCOO—)_2$, $((CH_3)_3COCOO—)_2$, $((CH_3)_3CO—)_2$, $((CH_3)_2CHOCOO—)_2$ or $((CH_3)_3CC_6H_{10}OCOO—)_2$ may be mentioned (wherein $C_6H_5$ is a phenyl group, $C_6F_5$ is a pentafluorophenyl group and $C_6H_{10}$ is a 1,4-cyclohexyl group).

The polymerization temperature and the polymerization pressure are not particularly limited. The polymerization temperature is preferably from 0 to 200° C. The polymerization pressure is preferably from atmospheric pressure to 10 MPa.

The polymer of the present invention is a polymer excellent in the water and oil repellency, heat resistance, mold release properties, chemical resistance, transparency, light resistance and low refractive index characteristic, and is a polymer soluble in an organic solvent.

A coating film or a film containing the polymer of the present invention is useful for applications to e.g. optical fiber materials, pericle materials, resist materials, lens materials or materials for a surface protective film of a display.

It is preferred that the coating film or the film containing the polymer of the present invention is obtained in such a manner that a solution composition obtained by dissolving the polymer of the present invention in an organic solvent is applied on the surface of a substrate, followed by drying to remove the organic solvent.

As a specific example of the organic solvent, an alcohol such as methanol, ethanol, propanol, butanol, pentanol, hexanol, cyclohexanol or pentanediol; a ketone such as acetone, methylisobutyl ketone or cyclohexanone; an acetate such as ethyl acetate or butyl acetate; an aromatic hydrocarbon such as toluene or xylene; a glycol ether such as propyleneglycol monomethyl ether or propyleneglycol monoethyl ether; a glycol ester such as propyleneglycol monomethyl ether acetate or carbitol acetate; a perfluorocarbon, a hydrofluorocarbon, a hydrochlorofluorocarbon, a perfluoroether, a fluoroalcohol, a fluoroketone, a hydrofluoroether, a fluorobenzene or a fluoroalkylbenzene may be mentioned.

The amount of the polymer of the present invention in the above solution composition, is preferably from 0.1 to mass %, particularly preferably from 5 to 15 mass % to the organic solvent. In such a case, it is possible to readily control the thickness of the coating film or the film containing the polymer of the present invention, and further the solution composition is stable.

As a method of applying the above solution composition on the surface of the substrate, it is possible to employ a known method such as roll coating, casting, dip coating, spin coating, water casting, dye coating or a Langmuir-Blodgett method.

EXAMPLES

Now, the present invention will be described in detail with reference to Examples, but it should be understood that the present invention is not limited thereto.

Gas chromatography will be referred to as GC, infrared spectroscopic spectrum as IR, the purity obtained from a peak area ratio as GC purity, tetramethylsilane as TMS, a gel permeation chromatography method as a GPC method, $CF_2ClCF_2CHFCl$ (dichloropentafluoropropane) as R-225 and hexafluoroisopropyl alcohol as HFIP. FC-77 is a fluorine-containing organic solvent.

A number average molecular weight will be referred to as Mn and a weight average molecular weight as Mw.

Example 1

Production Example for Compound ($2^1$)

To a flask maintained at 0° C., the following compound ($1^1$) (27.46 g), NaF (3.78) and acetone (100 mL) were added, followed by stirring. Then, water (1.14 g) was dropwise added to the flask over a period of 10 minutes. After completion of the dropwise addition, the interior of the flask was stirred at 25° C. for 5 hours. The solution in the flask was recovered by filtration, and dried over magnesium sulfate to obtain a crude product. Then, the crude product was purified by sublimation under reduced pressure (6.67 kPa) to obtain the following compound ($2^1$) (22.01 g). NMR data of the compound ($2^1$) is shown as follows:

$^1$H-NMR (300.4 MHz, CDCl$_3$, TMS) δ (ppm): 3.91 (dec, J=5.6 Hz)

$^{19}$F-NMR (282.7 MHz, CDCl$_3$, CFCl$_3$) δ (ppm): −108.7 (6F), −120.3 (3F), −121.7 (3F), −219.4 (3F)

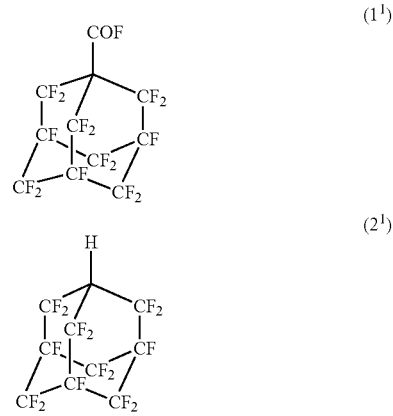

Example 2

Production Example for Compound ($3^1$)

To a mixture of the compound ($2^1$) (2.03 g) and dimethylsulfoxide (50 mL), potassium hydroxide (1.00 g) dissolved in a small amount of water and a 38 mass % aqueous formalin solution (20 mL) were added in this order at 25° C., followed by heating to 75° C. as it was. After completion of stirring for 6.5 hours, a 6 mol/L aqueous hydrochloric acid solution (3 mL) was added thereto. The reaction solution was dispersed in water (150 mL), followed by extraction with R-225 (40 mL), and the extract obtained was washed twice with water, followed by drying over magnesium sulfate. Further, the solvent was distilled off to obtain the following compound ($3^1$) (1.58 g). NMR data and IR data of the compound ($3^1$) are shown as follows:

$^1$H-NMR (300.4 MHz, CDCl$_3$, TMS) δ (ppm): 1.91 (s, 1H) 4.64 (s, 2H)

$^{19}$F-NMR (282.7 MHz, CDCl$_3$, CFCl$_3$) δ (ppm): −113.9 (6F), −121.2 (6F), −219.3 (3F)

IR (KBr) ν$_{max}$: 3359, 2975, 2918, 1272 cm$^{−1}$

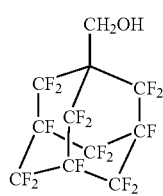

(3$^1$)

Example 3

Production Example for Compound (3$^2$)

The following compound (3$^2$) is obtained by carrying out a reaction under the same conditions as in Example 1 except that the compound (1$^1$) is changed to the following compound (1$^2$).

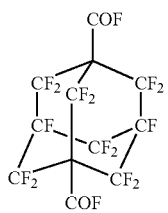

(1$^2$)

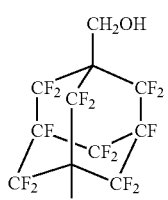

(3$^2$)

Example 4

Production Example for Compound (3$^3$)

The following compound (3$^3$) is obtained by carrying out a reaction under the same conditions as in Example 1 except that the compound (1$^1$) is changed to the following compound (1$^3$).

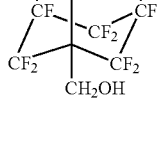

(1$^3$)

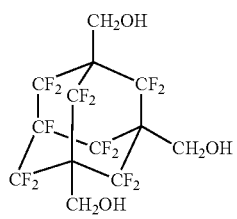

(3$^3$)

Example 5

Production Example for Compound (3$^4$)

The following compound (3$^4$) is obtained by carrying out a reaction under the same conditions as in Example 1 except that the compound (1$^1$) is changed to the following compound (1$^4$).

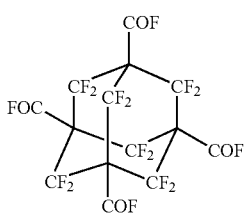

(1$^4$)

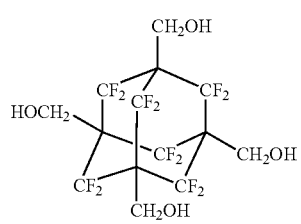

(3$^4$)

Example 6

Production Example for Compound (4$^1$)

To a flask, the compound (3$^1$) (6.01 g) and R-225 (103 g) were added. Then, to the flask, triethylamine (1.68 g) and CH$_2$=C(CH$_3$)COCl (1.58 g) were gradually added, and then the interior of the flask was stirred at 25° C. for 2 hours. A solution in the flask was filtrated, and a filtrate obtained was washed twice with water (50 mL). Then, the solution in the flask was dried over magnesium sulfate, followed by concentration to obtain a pale yellow solid material (6.19 g). The solid material was purified with a column chromatography to obtain the following compound (4$^1$)

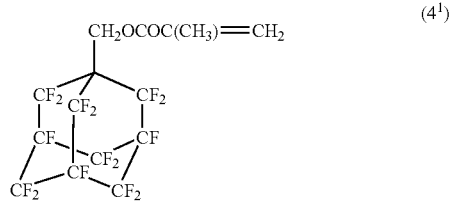

(4¹)

NMR data of the compound (4¹) is shown as follows:
$^1$H-NMR (300.4 MHz, CDCl$_3$, TMS) δ (ppm): 1.96 (s, 3H) 5.06 (s, 2H), 5.71 (s, 1H), 6.19 (s, 1H)
$^{19}$F-NMR (282.7 MHz, CDCl$_3$, CFCl$_3$) δ (ppm): −113.6 (6F), −121.1 (6F), −219.4 (3F)

Example 7

Example of Homopolymerization of Compound (4¹)

To a pressure resistant glass reactor (internal capacity 50 mL), the compound (4¹) (0.8 g) and F(CF$_2$)$_6$H (1.06 g) were added. Then, a solution of ((CH$_3$)$_2$CHOCOO—)$_2$ (0.28 g), which diluted to 50 mass % with R-225 was added thereto. After the interior of the reactor was freeze-deaerated, the reactor was sealed, and then the internal temperature of the reactor was kept at 40° C. for 18 hours to carry out polymerization reaction. After completion of the polymerization reaction, the solution in the reactor was dropwise added to methanol. A solid material flocculated was recovered, followed by vacuum-drying at 90° C. for 24 hours. As a result, a polymer (0.62 g) (hereinafter, referred to as a polymer (4h¹)) obtained by polymerization of the compound (4¹) was obtained. The polymer (4h') was a white powdery amorphous polymer at 25° C.

The molecular weight of the polymer (1 h) was measured by GPC using a mixed solvent containing 99 vol % of R-225 and 1 vol % of HFIP as a mobile phase, and using polymethyl methacrylate as internal standard. The polymer (4h¹) had Mn of 20,000 and Mw of 7,000. Further, the polymer (4h¹) had a contact angle of 107.80 and a falling angle of 7° to water.

Example 8

Example of Copolymerization of Compound (4¹) (1)

To a pressure resistant glass reactor (internal capacity 50 mL), the compound (4¹) (1.44 g), 2-ethyl-2-adamantyl acrylate (4.0 g), 2-oxotetrahydrofuran-3-yl methacrylate (0.8 g) and methyl ethyl ketone (10.32 g) were added. Then, a solution of ((CH$_3$)$_2$CHOCOO—)$_2$ (2.4 g) diluted to 50 mass % with dichloropentafluoropropane was added thereto. After the interior of the reactor was freeze-deaerated, the reactor was sealed, followed by polymerization reaction in the same manner as in Example 3-1 to obtain a polymer (4.9 g) (hereinafter, referred to as a polymer (4c¹)) by copolymerization of a compound (4¹), 2-ethyl-2-adamantyl acrylate and 2-oxotetrahydrofuran-3-yl methacrylate. The polymer (4c¹) was a white powdery amorphous polymer at 25° C.

The molecular weight of the polymer (4c¹) was measured by GPC using tetrahydrofuran as a mobile phase, and using polystyrene as internal standard. The polymer (4c¹) had Mn of 3,800 and Mw of 9,300. Further, the polymer (4c¹) was soluble in tetrahydrofuran, propylene glycol monomethyl ether acetate or cyclopentanone.

The polymer (4c¹) was analyzed by $^{19}$F-NMR and $^1$H-NMR, and as a result, the polymer (4c¹) was a polymer containing 11 mol % of repeating units of the compound (4¹), 67 mol % of repeating units of 2-ethyl-2-adamantyl methacrylate and 22 mol % of repeating units of 2-oxotetrahydrofuran-3-yl methacrylate, based on the total repeating units. Further, the polymer (4c¹) had a contact angle of 93.3° and a falling angle of 12° to water.

Example 9

Example of Copolymerization of Compound (4¹) (2)

To a pressure resistant glass reactor (internal capacity 50 mL), the compound (4¹) (0.68 g), 2-ethyl-2-adamantyl acrylate (4.0 g), 2-oxotetrahydrofuran-3-yl methacrylate (1.8 g) and methyl ethyl ketone (10.8 g) were added. Then, a solution of ((CH$_3$)$_2$CHOCOO—)$_2$ (2.6 g) diluted to 50 mass % with dichloropentafluoropropane was added thereto. After the interior of the reactor was freeze-deaerated, the reactor was sealed, followed by polymerization reaction in the same manner as in Example 3-1 to obtain a polymer (5.2 g) (hereinafter, referred to as a polymer (4c²)) obtained by copolymerization of a compound (4¹), 2-ethyl-2-adamantyl acrylate and 2-oxotetrahydrofuran-3-yl methacrylate. The polymer (4c²) was a white powdery amorphous polymer at 25° C.

The molecular weight of the polymer (4c²) was measured by GPC using tetrahydrofuran as a mobile phase, and using polystyrene as internal standard. The polymer (4c²) had Mn of 5,000 and Mw of 15,000. Further, the polymer (4c²) was soluble in tetrahydrofuran, propylene glycol monomethyl ether acetate or cyclopentanone.

The polymer (4c²) was analyzed by $^{19}$F-NMR and $^1$H-NMR, and as a result, the polymer (4c²) was a polymer containing 4 mol % of repeating units of the compound (4¹), 54 mol % of repeating units of 2-ethyl-2-adamantyl methacrylate and 42 mol % of repeating units of 2-oxotetrahydrofuran-3-yl methacrylate, based on the total repeating units. Further, the polymer (4c²) had a contact angle of 83.6° and a falling angle of 14° to water.

INDUSTRIAL APPLICABILITY

According to the present invention, it is possible to provide a novel polymerizable fluoroadamantane derivative, and a novel polymer excellent in the water and oil repellency, heat resistance, mold release properties, chemical resistance, transparency, light resistance and low refractive index characteristic. The polymer of the present invention is useful for optical fiber materials (a core material and a clad material for optical fibers), pericle materials, resist materials (e.g. a resist film material and a resist protective film material), lens materials (e.g. a lens for glasses, an optical lens and an optical cell), surface protective films for displays (e.g. PDP, LCD, CRT and FED) or the like.

The entire disclosures of Japanese Patent Application No. 2005-314801 filed on Oct. 28, 2005 and Japanese Patent Application No. 2006-045299 filed on Feb. 22, 2006 including specifications, claims and summaries are incorporated herein by reference in their entireties.

The invention claimed is:

1. A process for producing a compound represented by the following formula (p2), which comprises reacting a compound represented by the following formula (m1) with a protic nucleophile:

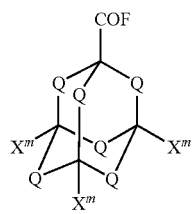

(m1)

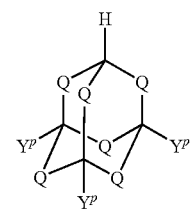

(p2)

provided that the symbols in the formulae have the following meanings:

Q: a monofluoromethylene group or a difluoromethylene group, provided that six Qs may be the same or different;

$X^m$: a hydrogen atom, a fluorine atom or a fluorocarbonyl group, provided that three $X^m$s may be the same or different; and $Y^p$: a group corresponding to each $X^m$, provided that $Y^p$ corresponding to $X^m$ which is a hydrogen atom, is a hydrogen atom, $Y^p$ corresponding to $X^m$ which is a fluorine atom, is a fluorine atom, and $Y^p$ corresponding to $X^m$ which is a fluorocarbonyl group, is a fluorocarbonyl group or a hydrogen atom.

2. The process for producing a compound according to claim 1, wherein the protic nucleophile is water.

3. A process for producing a compound represented by the following formula (p21), which comprises reacting a compound represented by the following formula (m11) with a protic nucleophile:

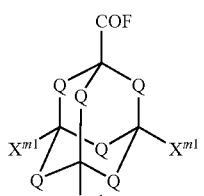

(m11)

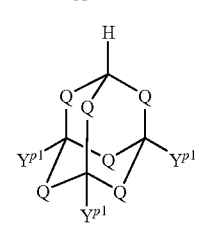

(p21)

provided that the symbols in the formulae have the following meanings:

Q: a monofluoromethylene group or a difluoromethylene group, provided that six Qs may be the same or different;

$X^{m1}$: a hydrogen atom or a fluorine atom, provided that three $X^{m1}$s may be the same or different; and $Y^{p1}$: a group corresponding to each $X^{m1}$, provided that $Y^{p1}$ corresponding to $X^{m1}$ which is a hydrogen atom, is a hydrogen atom, and $Y^{p1}$ corresponding to $X^{m1}$ which is a fluorine atom, is a fluorine atom.

4. The process for producing a compound according to claim 3, wherein the protic nucleophile is water.

5. A process for producing a compound represented by the following formula (p3), which comprises reacting a compound represented by the following formula (m2) with a compound represented by the formula W—CHO in the presence of a basic compound:

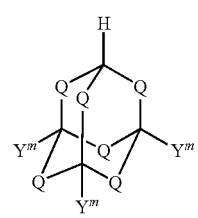

(m2)

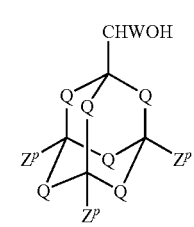

(p3)

provided that the symbols in the formulae have the following meanings:

Q: a monofluoromethylene group or a difluoromethylene group, provided that six Qs may be the same or different;

$Y^m$: a fluorine atom or a hydrogen atom, provided that three $Y^m$s may be the same or different;

$Z^p$: a group corresponding to each $Y^m$, provided that $Z^p$ corresponding to $Y^m$ which is a fluorine atom, is a fluorine atom, and $Z^p$ corresponding to $Y^m$ which is a hydrogen atom, is a hydrogen atom or a group represented by the formula —CHWOH; and W: a hydrogen atom or a $C_{1-10}$ monovalent hydrocarbon group.

6. A process for producing a compound represented by the following formula (p31), which comprises reacting a compound represented by the following formula (m21) with a compound represented by the formula W—CHO in the presence of a basic compound and a polar solvent:

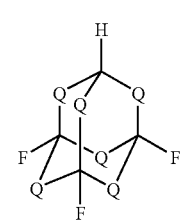

(m21)

-continued

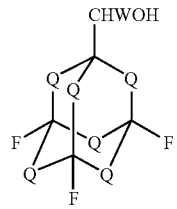
(p31)

provided that the symbols in the formulae have the following meanings:
Q: a monofluoromethylene group or a difluoromethylene group, provided that six Qs may be the same or different; and
W: a hydrogen atom or a $C_{1-10}$ monovalent hydrocarbon group.

7. A compound represented by the following formula (3):

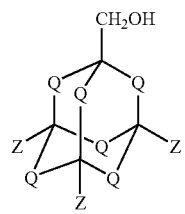
(3)

provided that the symbols in the formula have the following meanings:
Q: a monofluoromethylene group or a difluoromethylene group, provided that six Qs may be the same or different; and
Z: a fluorine atom, a hydrogen atom or a hydroxymethyl group, provided that three Zs may be the same or different.

8. A compound represented by the following formula (31):

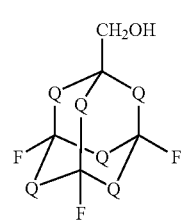
(31)

provided that the symbols in the formula have the following meanings:
Q: a monofluoromethylene group or a difluoromethylene group provided that six Qs may be the same or different.

9. A process for producing a compound represented by the following formula (p4), which comprises reacting a compound represented by the formula $CH_2=CRCOG$ with a compound represented by the following formula (m3):

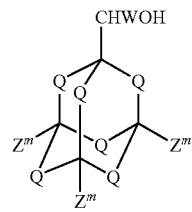
(m3)

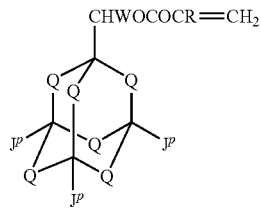
(p4)

provided that the symbols in the formulae have the following meanings:
G: a halogen atom;
W: a hydrogen atom or a $C_{1-10}$ monovalent hydrocarbon group;
R: a hydrogen atom, a fluorine atom, a methyl group or a trifluoromethyl group;
Q: a monofluoromethylene group or a difluoromethylene group, provided that six Qs may be the same or different;
$Z^m$: a hydrogen atom, a fluorine atom or a group represented by the formula —CHWOH, provided that three $Z^m$s may be the same or different; and
$J^p$: a group corresponding to each $Z^m$, provided that $J^p$ corresponding to $Z^m$ which is a hydrogen atom, is a hydrogen atom, $J^p$ corresponding to $Z^m$ which is a fluorine atom, is a fluorine atom, and $J^p$ corresponding to $Z^m$ which is a group represented by the formula —CHWOH, is a group represented by the formula —CHWOH or a group represented by the formula —CHWOCOCR=$CH_2$.

10. A compound represented by the following formula (4):

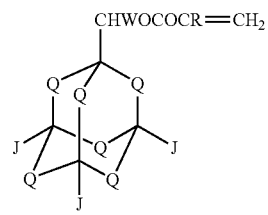
(4)

provided that the symbols in the formula have the following meanings:
W: a hydrogen atom or a $C_{1-10}$ monovalent hydrocarbon group;
R: a hydrogen atom, a fluorine atom, a methyl group or a trifluoromethyl group;
Q: a monofluoromethylene group or a difluoromethylene group, provided that six Qs may be the same or different; and
J: a hydrogen atom, a fluorine atom, a group represented by the formula —CHWOH or a group represented by the formula —CHWOCOCR=CH₂, provided that three Js may be the same or different.

11. A compound represented by the following formula (41):

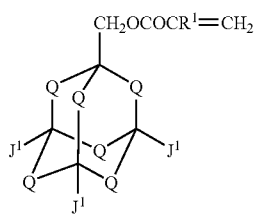
(41)

provided that the symbols in the formula have the following meanings:

R¹: a hydrogen atom or a methyl group;

Q: a monofluoromethylene group or a difluoromethylene group, provided that six Qs may be the same or different; and J¹: a hydrogen atom or a fluorine atom, provided that three J¹s may be the same or different.

12. A polymer obtained by polymerizing a compound represented by the following formula (4):

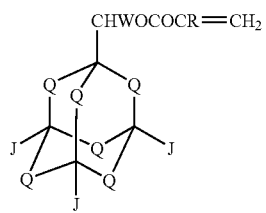
(4)

provided that the symbols in the formula have the following meanings:

W: a hydrogen atom or a $C_{1-10}$ monovalent hydrocarbon group;

R: a hydrogen atom, a fluorine atom, a methyl group or a trifluoromethyl group;

Q: a monofluoromethylene group or a difluoromethylene group, provided that six Qs may be the same or different; and J: a hydrogen atom, a fluorine atom, a group represented by the formula —CHWOH or a group represented by the formula —CHWCOCR=CH₂, provided that three Js may be the same or different.

13. The polymer according to claim 12, wherein the weight average molecular weight is from 1,000 to 1,000,000.

14. A polymer obtained by polymerizing a compound represented by the following formula (41):

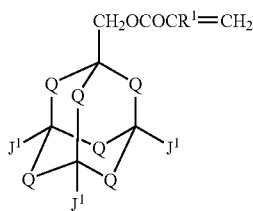
(41)

provided that the symbols in the formula have the following meanings:

R¹: a hydrogen atom or a methyl group;

Q; a monofluoromethylene group or a difluoromethylene group, provided that six Qs may be the same or different; and J¹: a hydrogen atom or a fluorine atom, provided that three J¹s may be the same or different.

15. The polymer according to claim 14, wherein the weight average molecular weight is from 1,000 to 1,000,000.

\* \* \* \* \*